United States Patent [19]
Sabalvaro, Jr.

[11] Patent Number: 5,667,292
[45] Date of Patent: Sep. 16, 1997

[54] HAT LIGHT

[76] Inventor: Valentin C. Sabalvaro, Jr., 3070 Allenwood Dr., San Jose, Calif. 95148

[21] Appl. No.: 433,152

[22] Filed: May 3, 1995

[51] Int. Cl.[6] ........................................ F21L 15/14
[52] U.S. Cl. .................. 362/106; 362/105; 2/10; 2/12; 2/209.13
[58] Field of Search ..................... 362/103, 105, 362/106; 2/10, 12, 209.13, 906

[56] References Cited

U.S. PATENT DOCUMENTS

| | | | |
|---|---|---|---|
| 2,421,643 | 6/1947 | Ostli | 362/106 |
| 2,533,626 | 12/1950 | Reiter | 2/10 |
| 2,765,398 | 10/1956 | Mays | 362/105 |
| 3,087,049 | 4/1963 | Schecter | 362/106 |
| 3,389,406 | 6/1968 | Mitchell | 2/12 |
| 3,830,230 | 8/1974 | Chester | 600/249 |
| 4,432,042 | 2/1984 | Zeller | 362/183 |
| 4,724,546 | 2/1988 | Cumbie, Jr. | 2/12 |
| 4,794,496 | 12/1988 | Lanes | 362/105 |
| 4,901,211 | 2/1990 | Shen | 362/106 |
| 4,916,596 | 4/1990 | Sharrah | 362/190 |
| 4,970,631 | 11/1990 | Marshall | 362/105 |
| 5,467,992 | 11/1995 | Harkness | 362/106 |

*Primary Examiner*—Alan Cariaso

[57] ABSTRACT

A portable light that is hands-free, out of the way, adjustable, and automatically directed to the user's line of sight by virtue of his head movement. This is accomplished by taking a topless hat, commonly known as the visor, and building around it to form a portable light that is worn on the head. Said visor would have battery casing molded at the base of the brim closest to the forehead to minimize the downward pull of the battery's weight. The bulb assembly housing unit is attached to the front of the brim by means to allow pivotal movement thus allowing for the light to he directed forward or downward, or at any angle in between.

2 Claims, 3 Drawing Sheets

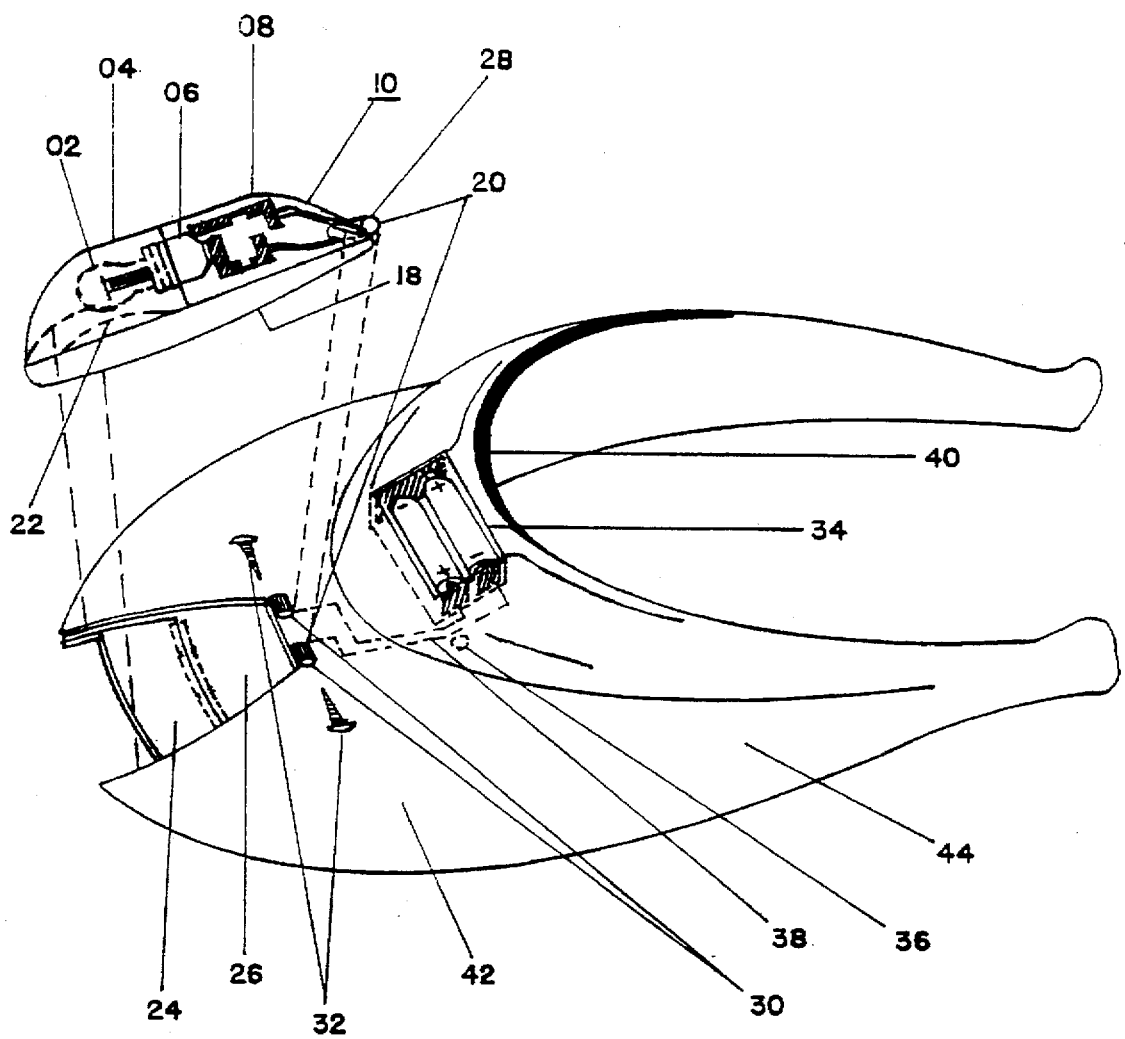
FIG. 2-A

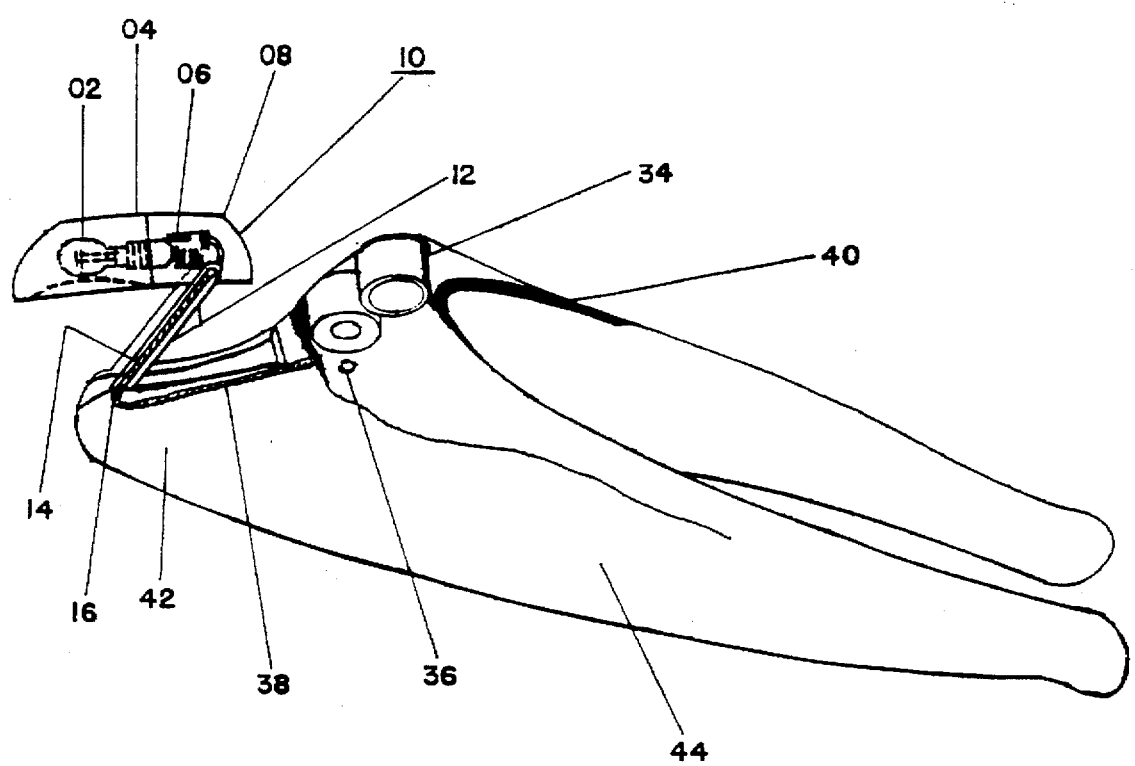
FIG. 2-B

HAT LIGHT

BACKGROUND

1. Field of Invention

This invention relates to a portable light that is worn on the head in the general shape and appearance of a topless hat, commonly known as the visor, used primarily for reading and other hand chores where localized, portable lighting is desired.

2. Description of Prior Art

Various types of portable lights are known in the prior art. There is one, in U.S. Pat. No. 4,432,042 (1984), that is clipped on to the book. It is lightweight, but an added weight to the book nonetheless. It also gets in the way when turning pages. Also, because it is stationary relative to the book, it does not provide uniform lighting to each little sections as one reads from left to right and top to bottom, particularly when reading a larger book.

Other prior arts, like the current invention, are worn on the head but with disadvantages. In U.S. Pat. No. 4,970,631 (1990), the flashlight is attached to the side of the head, which generally requires the person to view the object of interest out of the corner of the eye. Also, the Velcro attachment makes it less ideal for adjusting the light in a vertical plane. Others, as in U.S. Pat. No. 4,794,496 (1988), and U.S. Pat. No. 4,916,596 (1990), are mounted on the forehead with some kind of strap, but are unsightly because they are designed drastically different from anything a person would normally wear on the head. Still others, in U.S. Pat. No. 2,421,643 (1944), and U.S. Pat. No. 2,765,398 (1954), are mounted on top of the head with helmet and/or straps, and like the others are also unsightly. Another device, the Surgical Head lamp, U.S. Pat. No. 3,830,230 (1974), is so highly specialized, it is meant for use only by people in the medical surgical profession.

OBJECTS AND ADVANTAGES

An object of this invention is to provide a portable, out of the way, and hands-free light primarily for reading, although not limited to such specific use. Another object of this invention is to provide a portable light that is automatically directed to the user's line of sight. It is also an object of this invention to provide a portable light to be worn on the head without making it seem an unnatural object thereat and without causing glare to the eyes.

The current invention fulfills all the stated objectives and solves the many disadvantages of the prior arts. Being worn on the head, it leaves the hands free and does not get in the way when turning pages. The light is automatically directed to the user's line of sight by virtue of his head movement. When in an unused position, with the bulb assembly housing unit flushed against the brim, it appears much like a regular visor and can be carried around as such, providing for enhanced portability.

Two design alternatives are presented, both of which accomplish the objects of this invention:

The first, which is the preferred design and represented in FIG. 2-A, uses a cutout front center portion of the brim itself as the base for the bulb assembly housing unit. The unit is attached to the brim by means to allow pivotal movement. An adjustable eye shield, in the shape and contour of the brim, is attached to the underside of the brim to protect the eyes from glare when the device is in use.

On the second design which is represented in FIG. 2-B, the bulb assembly housing unit is attached to the brim with a pair of adjustable and extendible arms. The brim itself shields the eyes from glare when the device is in use.

BRIEF DESCRIPTION OF THE DRAWINGS

FIG. 2-A shows the current invention with the cutout front center section of the brim used as the base for the bulb assembly housing unit and equipped with an adjustable eye shield mounted at the underside of the brim.

FIG. 2-B shows the alternate design where the bulb assembly housing unit is mounted to the brim unit with adjustable arms.

REFERENCE NUMERALS

Figure 1:
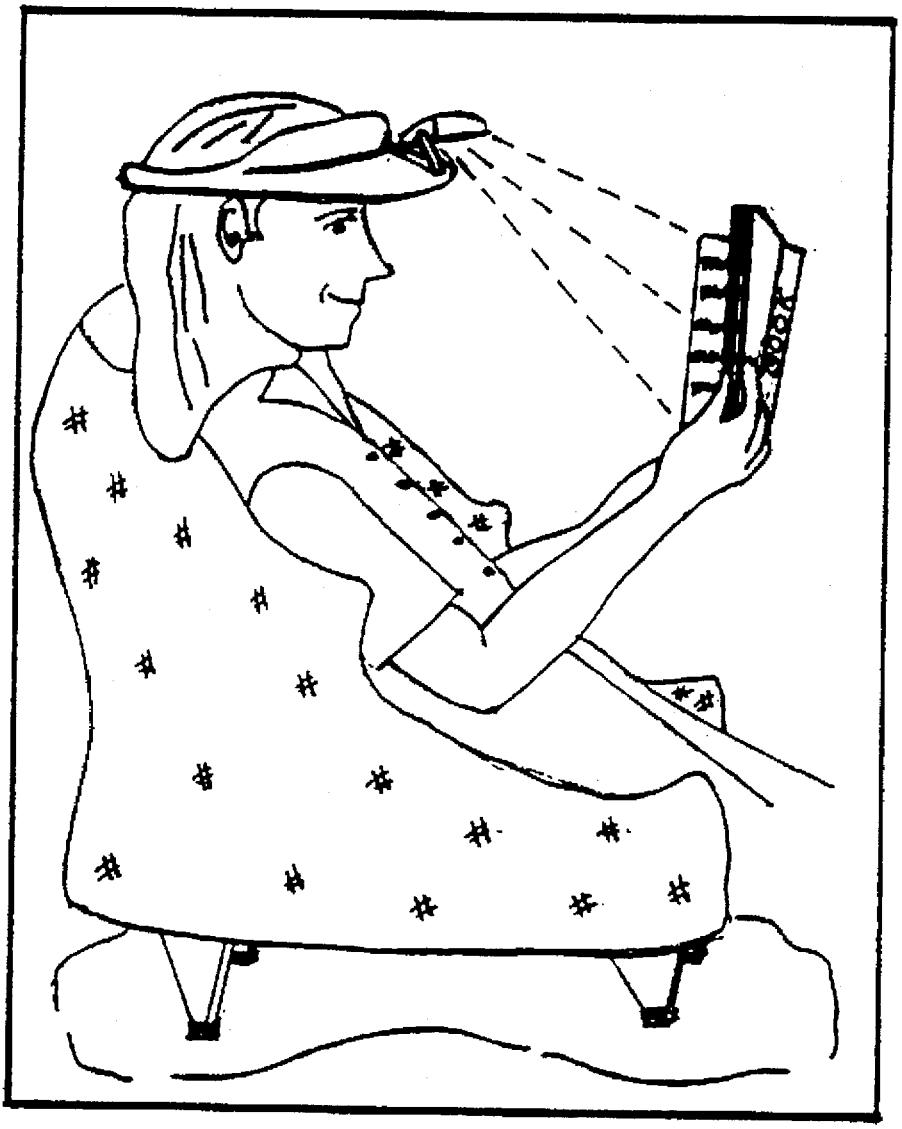
FIG. 1 shows how the current invention might be used.

02—Bulb
04—Bulb cover
06—Bulb assembly
08—Bulb assembly casing
10—Bulb assembly housing unit
12—Mounting arms
14—Electrical wires inside the arms
16—On/Off contact points (with arms)
18—Cutout section
20—On/Off contact points (with cutout section)
22—Base opening
24—Eye shield
26—Rest stop
28—Tubular mounting section at the Bulb Assembly Housing unit
30—tubular mounting section at the brim
32—Screws
34—Battery casing
36—Receptacle for connection to AC electrical outlet
38—Electrical wires
40—Anti-slip cushion

DESCRIPTION OF DRAWINGS

In FIG. 2-A, the cutout (18) front center section of the projecting front brim of a hat, forms the base of the bulb assembly housing unit (10). It has an opening (22) directly below the bulb (02) to let the light through. Molded on top is the casing (08), housing the bulb assembly inside. The unit (10) is attached to the brim thru threaded tubular section (28), mating to corresponding sections (30) at the brim unit and held together with screws (32) at both ends. Electrical contact points (20) at the attachment means are arranged to connect when the bulb assembly housing unit is lifted up and to disconnect when pressed down to the level of the brim thus serving as the on/off switch.

Covering about half of the gap left open by the cut section of the brim, is material molded with the visor and is slightly recessed, forming a rest stop (26) that prevents the bulb assembly housing unit (10) from sagging below the level of the brim. The eye shield (24) is attached to the underside of the brim by means to allow pivotal movement. It is shaped to the contour of the brim so that when folded up and pressed against the brim in an unused position, it blends with the brim, making it almost unnoticeable. When folded down in a used position, it shields the eyes from glare.

In FIG. 2-B, the bulb assembly housing unit (10) is attached to the brim with two arms (12), one on each side, allowing for the unit to he raised and adjusted forward or downward. Electrical wires (14) running inside the arms connect to the bulb assembly (06). Electrical contact points (16) at the brim attachment are arranged to connect when the arms are lifted up and to disconnect when pressed down to the level of the brim thus serving as the on/off switch. The brim itself shields the eyes from glare when the device is in use.

In both FIGS. 2-A and 2-B, the bulb cover (04) is detachable allowing for the bulb to be exposed for replacement purposes. The battery casing (34) is molded at the base of the brim closest to the forehead to minimize the downward pull caused by the weight of the batteries. It is equipped with receptacle (36) for connecting to electrical AC outlet via a transformer. Electrical wires (38) running from the battery case are hidden within the brim material. The anti-slip cushion (40) running along the part apposition to the forehead helps prevent the device from slipping down a person's head. The bulb would preferably be of the halogen type which provides high intensity illumination. Lightweight plastic would be the preferred material throughout.

I claim:

1. A portable lighting device worn on a head of a user and directed to a line of sight of the user by virtue of head movement of the user, used primarily for reading, comprising of:

a) a topless hat defining a headband means engaging the head of the user above the user's eyes and extending at least partially around the head for holding said portable lighting device in place, and a projecting front brim extending outwardly from said headband means at an area where said projecting front brim is connected to and start extending outwardly from said headband means defining a base of said projecting front brim, b) a bulb assembly housing unit attached to said projecting front brim of said topless hat by means to allow said bulb assembly housing unit to pivot up and down, c) a battery casing molded as part of said topless hat, where said battery casing is located at said base of said projecting front brim of said topless hat, wherein said battery casing includes batteries electrically connected to the bulb assembly housing unit for powering illumination thereof.

2. A portable lighting device according to claim 1 where an eye shield in the shape and contour of said projecting front brim is attached to an underside and approximately middle section of said projecting front brim, whereby said eye shield protects the user's eyes from glare when folded down in a used position and blends with said projecting front brim when folded up in an unused position.

* * * * *

UNITED STATES PATENT AND TRADEMARK OFFICE
CERTIFICATE OF CORRECTION

PATENT NO. : 5,667,292

DATED : September 16, 1997

INVENTOR(S) : Valentin C. Sabalvaro, Jr.

It is certified that error appears in the above-identified patent and that said Letters Patent is hereby corrected as shown below:

Columns 1-4 should be deleted to appear as per attached.

Signed and Sealed this

Seventeenth Day of February, 1998

Attest:

BRUCE LEHMAN

Attesting Officer     *Commissioner of Patents and Trademarks*

HAT LIGHT

BACKGROUND

1. Field of Invention

This invention relates to a portable light that is worn on the head in the general shape and appearance of a topless hat, commonly known as the visor, used primarily for reading and other hand chores where localized, portable lighting is desired.

2. Description of Prior Art

Various types of portable lights are known in the prior art. There is one, in U.S. Pat. No. 4,432,042 (1984), that is clipped on to the book. It is lightweight, but an added weight to the book nonetheless. It also gets in the way when turning pages. Also, because it is stationary relative to the book, it does not provide uniform lighting to each little sections as one reads from left to right and top to bottom, particularly when reading a larger book.

Other prior arts, like the current invention, are worn on the head but with disadvantages. In U.S. Pat. No. 4,970,631 (1990), the flashlight is attached to the side of the head, which generally requires the person to view the object of interest out of the corner of the eye. Also, the Velcro attachment makes it less ideal for adjusting the light in a vertical plane. Others, as in U.S. Pat. No. 4,794,496 (1988), and U.S. Pat. No. 4,916,596 (1990), are mounted on the forehead with some kind of strap, but are unsightly because they are designed drastically different from anything a person would normally wear on the head. Still others, in U.S. Pat. No. 2,421,643 (1944), and U.S. Pat. No. 2,765,398 (1954), are mounted on top of the head with helmet and/or straps, and like the others are also unsightly. Another device, the Surgical Head lamp, U.S. Pat. No. 3,830,230 (1974), is so highly specialized, it is meant for use only by people in the medical surgical profession.

Two prior arts in U.S. Pat. No. 1,744,777 (1930) and U.S. Pat. No. 4,991,068 (1991), both make use of baseball style hats; that is, with both the crown portion and the bill portion. The crown portion presses down on the user's hair thus disturbing their hair style.

Others in U.S. Pat. Nos. 3,302,018 (1967), 4,090,232 (1978), and 4,530,112 (1985), all make use of helmet style caps making them unsuitable for wear and use for ordinary reading situations.

SUMMARY

An object of this invention is to provide a portable, out of the way, and hands-free light primarily for reading, although not limited to such specific use. Another object of this invention is to provide a portable light that is automatically directed to the user's line of sight. It is also an object of this invention to provide a portable light to he worn on the head without making it seem an unnatural object thereat and without causing glare to the eyes.

The current invention fulfills all the stated objectives and solves the many disadvantages of the prior arts. Being worn on the head, it leaves the hands free and does not get in the way when turning pages. The light is automatically directed to the user's line of sight by virtue of his head movement. When in an unused position, with the bulb assembly housing unit flushed against the brim, it appears much like a regular visor and can be carried around as such, providing for enhanced portability.

Two design alternatives are presented, both of which accomplish the objects of this invention:

The first, which is the preferred design and represented in FIG. 2-A, uses a cutout front center portion of the projecting front brim of a topless hat itself as the base for the bulb assembly housing unit. Said bulb assembly housing unit is attached to the brim by means to allow said bulb assembly housing unit to pivot up and down. An adjustable eye shield, in the shape and contour of the brim, and made of opaque material, is attached to the underside of the brim to protect the eyes from glare when the device is in use.

On the second design which is represented in FIG. 2-B, the bulb assembly housing unit is attached to the brim with a pair of adjustable and extendible arms. The brim itself shields the eyes from glare when the device is in use.

BRIEF DESCRIPTION OF THE DRAWINGS

FIG. 1 shows how the current invention might be used.

FIG. 2-A shows the current invention with the cutout front center section of the brim used as the base for the bulb assembly housing unit and equipped with an adjustable eye shield mounted at the underside of the brim.

FIG. 2-B shows the alternate design where the bulb assembly housing unit is mounted to the brim unit with adjustable arms.

Reference Numerals

02—Bulb
04—Bulb cover
06—Bulb assembly
08—Bulb assembly casing
10—Bulb assembly housing unit
12—Mounting arms
14—Electrical wires inside the arms
16—On/Off contact points (with arms)
18—Cutout section
20—On/Off contact points (with cutout section)
22—Base opening
24—Eye shield
26—Rest stop
28—Tubular mounting section at the Bulb Assembly Housing unit
30—tubular mounting section at the brim
32—Screws
34—Battery casing
36—Receptacle for connection to AC electrical outlet
38—Electrical wires
40—Anti-slip cushion
42—Projecting front brim
44—Topless hat (commonly known as the visor)

DESCRIPTION OF PREFERRED EMBODIMENTS

In FIG. 2-A, a cutout front center section 18 of a projecting front brim 42 of a topless hat 44, forms the base of a bulb assembly housing unit 10. Such topless hat 44 is commonly known as the visor. Bulb assembly housing unit 10 has an opening 22 directly below a bulb 02 to let the light through. Molded on top of cutout section 18 is a casing 08, housing a bulb assembly 06 inside. Bulb assembly housing unit 10 is attached to said brim 42 thru threaded tubular section 28, mating to corresponding sections 30 at the brim unit and held together with screws 32 at both ends. Electrical contact points 20 at the attachment means are arranged to connect when bulb assembly housing unit 10 is lifted up and to disconnect when pressed down to the level of the brim thus serving as the on/off switch.

Covering about half of the gap left open by the cut section of the brim, is material molded with said topless hat 44, and is slightly recessed, forming a rest stop 26 that prevents bulb assembly housing unit 10 from sagging below the level of brim 42. An eye shield 24 made of opaque material is attached to the underside of brim 42 by means to allow said eye shield 24 to pivot up and down. Eye shield 24 is shaped to the contour of brim 42 so that when folded up and pressed against said brim in an unused position, said eye shield blends with said brim, making it almost unnoticeable. When eye shield 24 is folded down in a used position, it shields the eyes from glare emitting from bulb 02.

In FIG. 2-B, bulb assembly housing unit 10 is attached to projecting front brim 42 of topless hat 44 with two arms 12, one on each side, allowing for bulb assembly housing unit 10 to be raised and adjusted forward or downward. Electrical wires 14 running inside arms 12 connect to bulb assembly 06. Electrical contact points 16 at the brim attachment are arranged to connect when arms 12 are lifted up and to disconnect when pressed down to the level of the brim thus serving as the on/off switch. Said brim 42 itself shields the eyes from glare emitting from bulb 02, when the device is in use.

In both FIGS. 2-A and 2-B, topless hat 44 forms the basis for holding the device adequately secure on a person's head. A battery casing 34 is molded at the base of brim 42 closest to the forehead to minimize the downward pull caused by the weight of the batteries. Battery casing 34 is equipped with receptacle 36 for connecting to electrical AC outlet via a transformer. Electrical wires 38 running from battery case 34 are hidden within the brim material. An anti-slip cushion 40 made of soft rubbery material running along the part apposition to the forehead helps prevent the device from slipping down a person's head and likewise provide cushion. A bulb cover 04 is detachable allowing for bulb 02 to be exposed for replacement purposes. The bulb would preferably be of the halogen or krypton type which provides high intensity illumination. Lightweight plastic would be the preferred material throughout.

I claim:

1. A portable lighting device worn on a head of a user and directed to a line of sight of the user by virtue of head movement of the user, used primarily for reading, comprising of:

a) a topless hat defining a headband means engaging the head of the user above the user's eyes and extending at least partially around the head for holding said portable lighting device in place, and a projecting front brim extending outwardly from said headband means at an area where said projecting front brim is connected to and start extending outwardly from said headband means defining a base of said projecting front brim, b) a bulb assembly housing unit attached to said projecting front brim of said topless hat by means to allow said bulb assembly housing unit to pivot up and down, (c) a battery casing molded as part of said topless hat, where said battery casing is located at said base of said projecting front brim of said topless hat, wherein said battery casing includes batteries electrically connected to the bulb assembly housing unit for powering illumination thereof.

2. A portable lighting device according to claim 1 where an eye shield in the shape and contour of said projecting front brim is attached to an underside and approximately middle section of said projecting front brim, whereby said eye shield protects the user's eyes from glare when folded down in a used position and blends with said projecting front brim when folded up in an unused position.

* * * * *